US012638437B2

(12) United States Patent
Lin et al.

(10) Patent No.: US 12,638,437 B2
(45) Date of Patent: May 26, 2026

(54) FABRIC FEATURE PREDICTING METHOD

(71) Applicant: TAIWAN TEXTILE RESEARCH INSTITUTE, New Taipei City (TW)

(72) Inventors: Hung-Yu Lin, New Taipei City (TW);
Pei-Te Shen, New Taipei City (TW);
Chin-Lun Chu, New Taipei City (TW);
Tzu-Yu Chiu, New Taipei City (TW);
Yu-Sian Ciou, New Taipei City (TW)

(73) Assignee: TAIWAN TEXTILE RESEARCH INSTITUTE, New Taipei City (TW)

( * ) Notice: Subject to any disclaimer, the term of this patent is extended or adjusted under 35 U.S.C. 154(b) by 453 days.

(21) Appl. No.: 18/500,258

(22) Filed: Nov. 2, 2023

(65) Prior Publication Data

US 2024/0151707 A1 May 9, 2024

(30) Foreign Application Priority Data

Nov. 3, 2022 (TW) .................................. 111142056

(51) Int. Cl.
*G01N 33/36* (2006.01)
(52) U.S. Cl.
CPC .................................... *G01N 33/36* (2013.01)
(58) Field of Classification Search
CPC .............................. G01N 33/36; G01N 33/367
See application file for complete search history.

(56) References Cited

U.S. PATENT DOCUMENTS

| | | | | |
|---|---|---|---|---|
| 2013/0325398 A1* | 12/2013 | Nakagawa | ............. | G01N 19/02 |
| | | | | 702/170 |
| 2019/0259192 A1 | 8/2019 | Ebrahimi et al. | | |
| 2022/0391547 A1* | 12/2022 | Bhatnagar | ............. | D04B 37/02 |

FOREIGN PATENT DOCUMENTS

CN 106909763 A 6/2017

* cited by examiner

*Primary Examiner* — Nathaniel J Kolb
(74) *Attorney, Agent, or Firm* — McClure, Qualey & Rodack, LLP

(57) ABSTRACT

A fabric feature predicting method includes following operations: measuring multiple first fabrics to generate multiple first fabric actual feature value groups; storing the first fabric actual feature value groups and multiple first fabric information groups of the first fabrics; selecting multiple third fabrics from the first fabrics according to a second fabric information group of a second fabric; generating at least one equation according to multiple third fabric actual feature value groups of the third fabrics and multiple third fabric information groups of the third fabrics; generating a second fabric predicted feature value group of the second fabric according to the at least one equation and the second fabric information group. The first fabric actual feature value groups include the third fabric actual feature value groups. The first fabric information groups include the third fabric information groups.

9 Claims, 5 Drawing Sheets

100

100

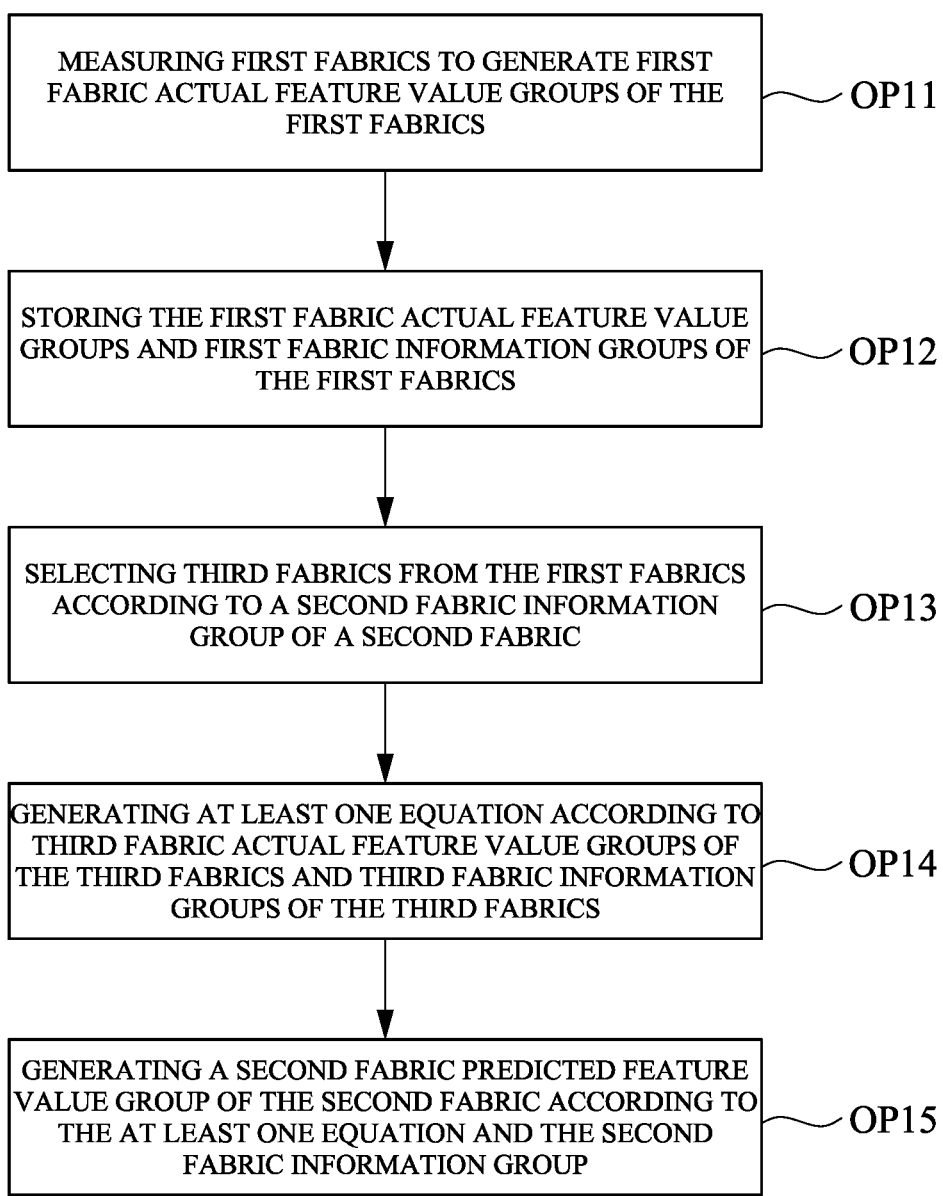

MEASURING FIRST FABRICS TO GENERATE FIRST
FABRIC ACTUAL FEATURE VALUE GROUPS OF THE
FIRST FABRICS ⟩— OP11

STORING THE FIRST FABRIC ACTUAL FEATURE VALUE
GROUPS AND FIRST FABRIC INFORMATION GROUPS OF
THE FIRST FABRICS ⟩— OP12

SELECTING THIRD FABRICS FROM THE FIRST FABRICS
ACCORDING TO A SECOND FABRIC INFORMATION
GROUP OF A SECOND FABRIC ⟩— OP13

GENERATING AT LEAST ONE EQUATION ACCORDING TO
THIRD FABRIC ACTUAL FEATURE VALUE GROUPS OF
THE THIRD FABRICS AND THIRD FABRIC INFORMATION
GROUPS OF THE THIRD FABRICS ⟩— OP14

GENERATING A SECOND FABRIC PREDICTED FEATURE
VALUE GROUP OF THE SECOND FABRIC ACCORDING TO
THE AT LEAST ONE EQUATION AND THE SECOND
FABRIC INFORMATION GROUP ⟩— OP15

COMPARING THE SECOND FABRIC INFORMATION GROUP AND THE FIRST FABRIC INFORMATION GROUPS — OP21

COMPARING A DISTANCE BETWEEN THE SECOND FABRIC INFORMATION GROUP AND ONE OF THE FIRST FABRIC INFORMATION GROUPS IN A VECTOR SPACE — OP23

SELECTING, IN THE FIRST FABRICS, A PART CLOSEST TO THE SECOND FABRIC INFORMATION GROUP AS THE THIRD FABRICS — OP22

OP14

GENERATING N STRAIGHT LINES ACCORDING TO THE
THIRD FABRIC INFORMATION GROUPS AND THE THIRD      OP31
FABRIC ACTUAL FEATURE VALUE GROUPS

GENERATING ONE OF THE AT LEAST ONE EQUATION
ACCORDING TO N SLOPES OF THE N STRAIGHT LINES      OP32

OP31

FABRIC FEATURE PREDICTING METHOD

CROSS-REFERENCE TO RELATED APPLICATION

This application claims priority to Taiwan Application Serial Number 111142056, filed Nov. 3, 2022, which is herein incorporated by reference in its entirety.

BACKGROUND

Technical Field

The present disclosure relates to a fabric feature predicting technology. More particularly, the present disclosure relates to a fabric feature predicting method.

Description of Related Art

Fabric information cannot present physical features of fabrics; in order to know fabric features, manual measurements must be performed to the fabrics; the manual measurements have higher costs and consume longer time. Thus, techniques associated with the development for overcoming problems described above are important issues in the field.

SUMMARY

The present disclosure provides a fabric feature predicting method. The fabric feature predicting method includes following operations: measuring multiple first fabrics to generate multiple first fabric actual feature value groups of the first fabrics; storing the first fabric actual feature value groups and multiple first fabric information groups of the first fabrics; selecting multiple third fabrics from the first fabrics according to a second fabric information group of a second fabric; generating at least one equation according to multiple third fabric actual feature value groups of the third fabrics and multiple third fabric information groups of the third fabrics; generating a second fabric predicted feature value group of the second fabric according to the at least one equation and the second fabric information group. The first fabric actual feature value groups include the third fabric actual feature value groups. The first fabric information groups include the third fabric information groups.

It is to be understood that both the foregoing general description and the following detailed description are by examples, and are intended to provide further explanation of the disclosure as claimed.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 1 is a flowchart diagram of a fabric feature predicting method illustrated according to one embodiment of this disclosure.

DETAILED DESCRIPTION

Figure 2:
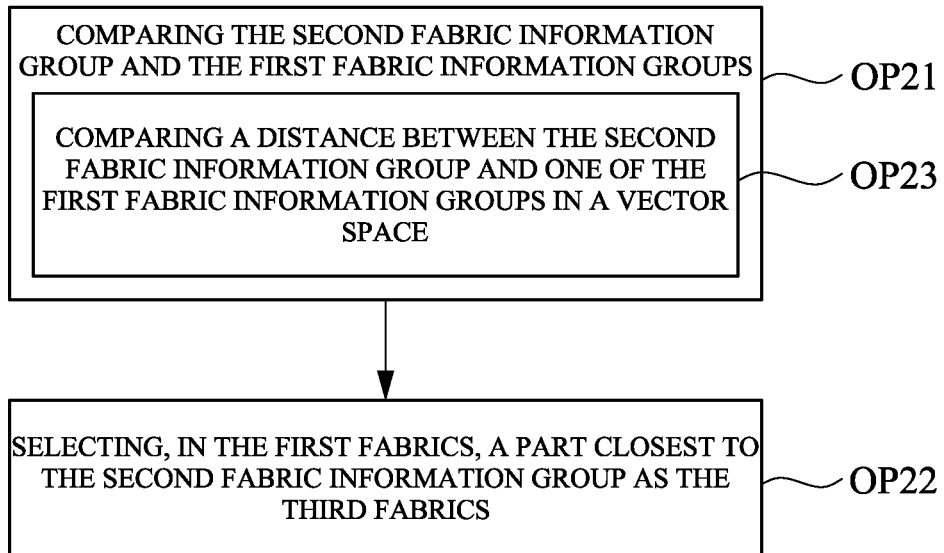
FIG. 2 is a flowchart diagram of further details of operations of the fabric feature predicting method illustrated according to one embodiment of this disclosure.

In the present disclosure, although the terms "first", "second", and the like are used in the present disclosure to describe different elements, the terms are used only to distinguish the elements or operations described in the same technical terms. The use of the term is not intended to be a limitation of the present disclosure.

Unless otherwise defined, all terms (including technical and scientific terms) used in the present disclosure have the same meaning as commonly understood by the ordinary skilled person to which the concept of the present invention belongs. It will be further understood that terms (such as those defined in commonly used dictionaries) should be interpreted as having a meaning consistent with its meaning in the related technology and/or the context of this specification and not it should be interpreted in an idealized or overly formal sense, unless it is clearly defined as such in this article.

The terms used in the present disclosure are only used for the purpose of describing specific embodiments and are not intended to limit the embodiments. As used in the present disclosure, the singular forms "a", "one" and "the" are also intended to include plural forms, unless the context clearly indicates otherwise. It will be further understood that when used in this specification, the terms "comprises (comprising)" and/or "includes (including)" designate the existence of stated features, steps, operations, elements and/or components, but the existence or addition of one or more other features, steps, operations, elements, components, and/or groups thereof are not excluded.

Hereinafter multiple embodiments of the present disclosure will be disclosed with schema, as clearly stated, the details in many practices it will be explained in the following description. It should be appreciated, however, that the details in these practices is not applied to limit the present disclosure. Also, it is to say, in some embodiments of the present disclosure, the details in these practices are non-essential. In addition, for the sake of simplifying schema, some known usual structures and element in the drawings by a manner of simply illustrating for it.

FIG. 1 is a flowchart diagram of a fabric feature predicting method 100 illustrated according to one embodiment of this disclosure. As illustratively shown in FIG. 1, the fabric feature predicting method 100 includes operations OP11-OP15; in some embodiments, the operations OP11-OP15 are performed in order; in some embodiments, the operations OP11-OP15 may be performed by a processor and a memory.

At the operation OP11, measuring multiple first fabrics to generate multiple first fabric actual feature value groups of the first fabrics. At the operation OP12, storing the first fabric actual feature value groups and multiple first fabric information groups of the first fabrics. At the operation OP13, selecting multiple third fabrics from the first fabrics according to a second fabric information group of a second fabric. At the operation OP14, generating at least one equation according to multiple third fabric actual feature value groups of the third fabrics and multiple third fabric information groups of the third fabrics. At the operation OP15, generating a second fabric predicted feature value group of the second fabric according to the at least one equation and the second fabric information group.

In some approaches, in order to know fabric features, manual measurements must be performed to the fabrics, such that costs are higher and consumed time is longer.

Compared to the above approaches, in some embodiments of the present disclosure, equations are generated according to the known third fabrics, and calculations are performed according to the equations and the second fabric information group. Under a condition without measuring the second fabric, the second fabric predicted feature value group of the second fabric may be obtained. As a result, the costs of manual measurements are reduced, and the second fabric predicted feature value group may be provided to customers as a reference.

In some embodiments, the first fabric actual feature value groups include the third fabric actual feature value groups. The first fabric information groups include the third fabric information groups.

In some embodiments, each of the first fabric information groups includes a main yarn percentage, a fabric weight and a drape coefficient of a corresponding one of the first fabrics. Each of the third fabric information groups includes a main yarn percentage, a fabric weight and a drape coefficient of a corresponding one of the third fabrics.

In some embodiments, the second fabric information group includes a main yarn percentage, a fabric weight and a drape coefficient of the second fabric.

In some embodiments, each of the first fabric actual feature value groups includes at least one of an actual meridional bending average stiffness, an actual zonal bending average stiffness, an actual meridional bending work, an actual zonal bending work, an actual thickness, an actual compression work, an actual compression recovery rate, an actual compression average stiffness, an actual recovery average stiffness, an actual thermal conductivity of compression, an actual thermal conductivity of recovery, an actual maximal heat flow, an actual meridional surface friction coefficient, an actual zonal surface friction coefficient, an actual meridional surface rough amplitude, an actual zonal surface rough amplitude, an actual meridional surface rough wavelength, an actual zonal surface rough wavelength of a corresponding one of the first fabrics.

In some embodiments, each of the third fabric actual feature value groups includes at least one of an actual meridional bending average stiffness, an actual zonal bending average stiffness, an actual meridional bending work, an actual zonal bending work, an actual thickness, an actual compression work, an actual compression recovery rate, an actual compression average stiffness, an actual recovery average stiffness, an actual thermal conductivity of compression, an actual thermal conductivity of recovery, an actual maximal heat flow, an actual meridional surface friction coefficient, an actual zonal surface friction coefficient, an actual meridional surface rough amplitude, an actual zonal surface rough amplitude, an actual meridional surface rough wavelength, an actual zonal surface rough wavelength of a corresponding one of the third fabrics.

In some embodiments, the second fabric predicted feature value group includes at least one of a predicted meridional bending average stiffness, a predicted zonal bending average stiffness, a predicted meridional bending work, a predicted zonal bending work, a predicted thickness, a predicted compression work, a predicted compression recovery rate, a predicted compression average stiffness, a predicted recovery average stiffness, a predicted thermal conductivity of compression, a predicted thermal conductivity of recovery, a predicted maximal heat flow, a predicted meridional surface friction coefficient, a predicted zonal surface friction coefficient, a predicted meridional surface rough amplitude, a predicted zonal surface rough amplitude, a predicted meridional surface rough wavelength, a predicted zonal surface rough wavelength of the second fabrics.

FIG. 2 is a flowchart diagram of further details of the operation OP13 of the fabric feature predicting method 100 illustrated according to one embodiment of this disclosure. As illustratively shown in FIG. 2, the operation OP13 includes operations OP21-OP22. In some embodiments, the operations OP21-OP22 are performed in order. The operation OP21 includes OP23. In some embodiments, the operations OP21-OP23 may be performed by the processor and the memory.

At the operation OP21, comparing the second fabric information group and the first fabric information groups. At the operation OP22, selecting, in the first fabrics, a part closest to the second fabric information group as the third fabrics. At the operation OP23, comparing a distance between the second fabric information group and one of the first fabric information groups in a vector space. In some embodiments, three axes of the vector space described above correspond to a main yarn percentage, a fabric weight and a drape coefficient, respectively.

Figure 3:
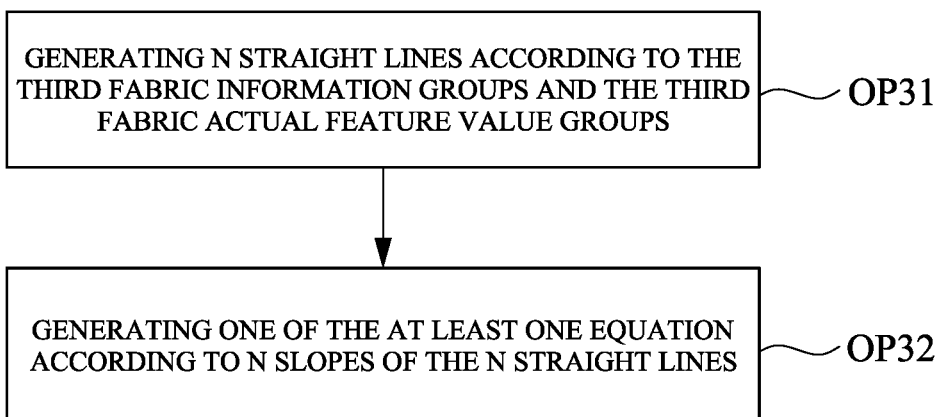
FIG. 3 is a flowchart diagram of further details of operations of the fabric feature predicting method illustrated according to one embodiment of this disclosure.

FIG. 3 is a flowchart diagram of further details of the operation OP14 of the fabric feature predicting method 100 illustrated according to one embodiment of this disclosure. As illustratively shown in FIG. 3, the operation OP14 includes operations OP31-OP32. In some embodiments, the operations OP31-OP32 are performed in order. In some embodiments, the operations OP31-OP32 may be performed by the processor and the memory.

At the operation OP31, generating N straight lines according to the third fabric information groups and the third fabric actual feature value groups. At the operation OP32, generating one of the at least one equation described above according to N slopes of the N straight lines, in which N is a positive integer.

Figure 4:
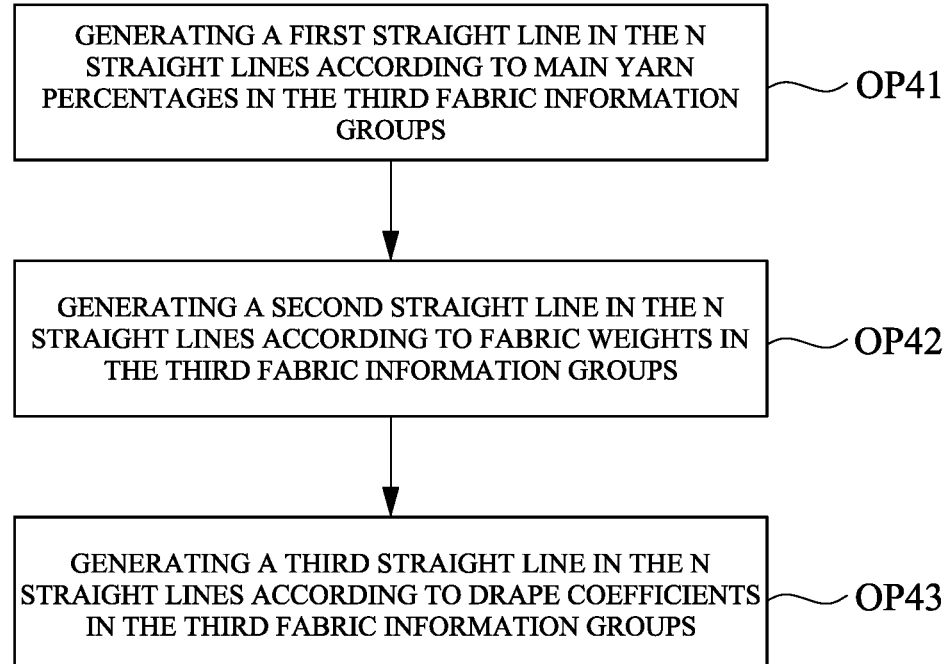
FIG. 4 is a flowchart diagram of further details of operations of the fabric feature predicting method illustrated according to one embodiment of this disclosure.

FIG. 4 is a flowchart diagram of further details of the operation OP31 of the fabric feature predicting method 100 illustrated according to one embodiment of this disclosure. As illustratively shown in FIG. 4, the operation OP31 includes operations OP41-OP43. In some embodiments, the operations OP41-OP43 can be performed in order or be performed simultaneously. In some embodiments, the operations OP41-OP43 may be performed by the processor and the memory.

At the operation OP41, generating a first straight line L1 in the N straight lines according to main yarn percentages in the third fabric information groups. At the operation OP42, generating a second straight line L2 in the N straight lines according to fabric weights in the third fabric information groups. At the operation OP43, generating a third straight line L3 in the N straight lines according to drape coefficients in the third fabric information groups. Details associated with the first straight line L1, the second straight line L2 and the third straight line L3 are described below with the embodiments associated with FIG. 5.

Figure 5:
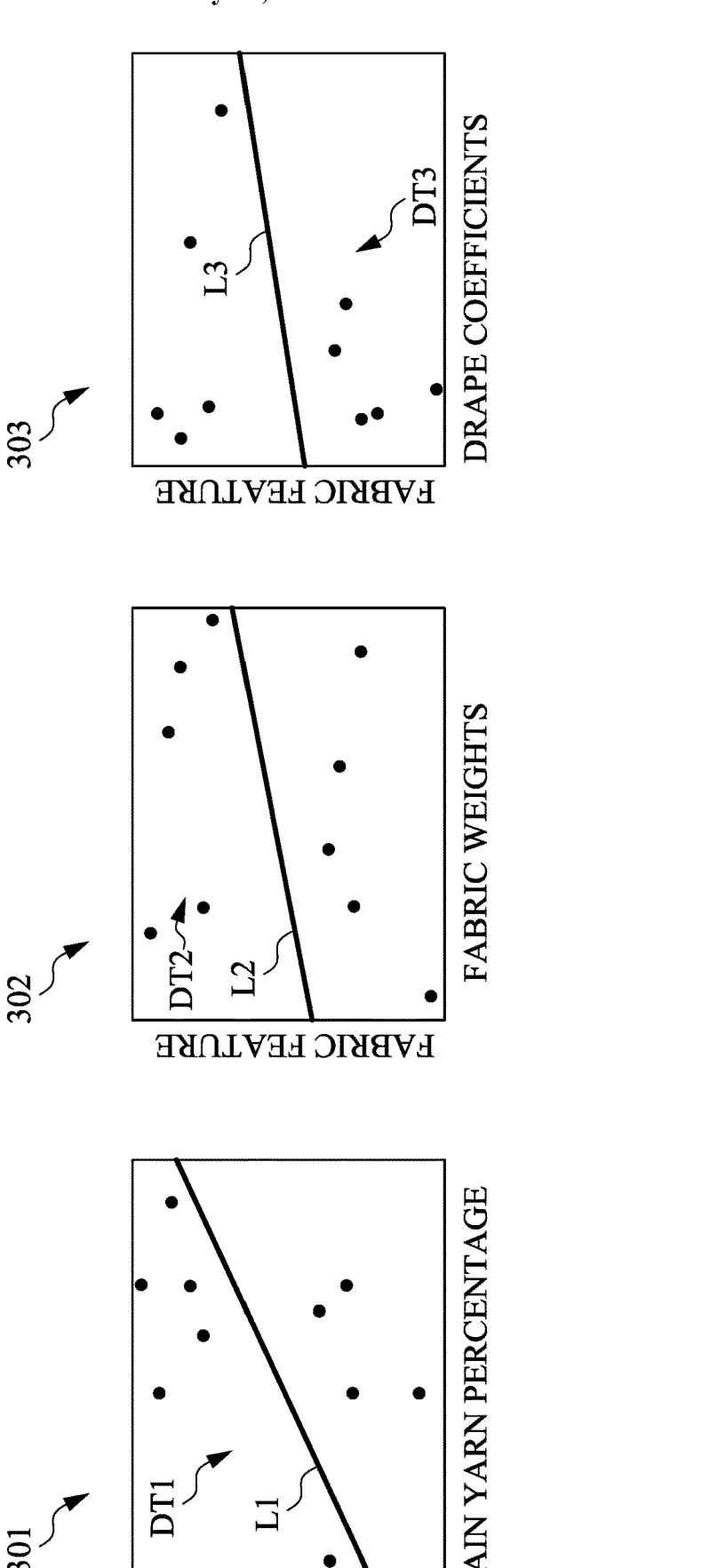
FIG. 5 is a schematic diagram of straight lines associated with the fabric feature predicting method illustrated according to one embodiment of this disclosure.

FIG. 5 is schematic diagrams 301-303 of straight lines associated with the fabric feature predicting method 100 illustrated according to one embodiment of this disclosure. As illustratively shown in FIG. 5, the schematic diagram 301 includes the first straight line L1 and first data points DT1. The schematic diagram 302 includes the second straight line L2 and second data points DT2. The schematic diagram 303 includes the third straight line L3 and third data points DT3.

In some embodiments, horizontal axes of the schematic diagrams 301-303 correspond to main yarn percentages, fabric weights and drape coefficients, respectively. Vertical axes of the schematic diagrams 301-303 correspond to a fabric feature, such as one of a meridional bending average stiffness, a zonal bending average stiffness, a meridional bending work, a zonal bending work, a thickness, a compression work, a compression recovery rate, a compression average stiffness, a recovery average stiffness, a thermal conductivity of compression, a thermal conductivity of recovery, a maximal heat flow, a meridional surface friction coefficient, a zonal surface friction coefficient, a meridional surface rough amplitude, a zonal surface rough amplitude, a meridional surface rough wavelength, a zonal surface rough wavelength.

In some embodiments, the first data points DT1 represents a relationship between the main yarn percentages of the third fabric information groups and the fabric feature described above. The second data points DT2 represents a relationship between the fabric weights of the third fabric information groups and the fabric feature described above. The third data points DT3 represents a relationship between the drape coefficients of the third fabric information groups and the fabric feature described above.

In some embodiments, the processor performs a regression analysis to the first data points DT1, to generate the first straight line L1, performs a regression analysis to the second data points DT2, to generate the second straight line L2, and performs a regression analysis to the third data points DT3, to generate the third straight line L3.

In some embodiments, one of the at least one equation described by the operation OP32 shown in FIG. 3 can be represented as following:

$$PD1 = K1 \times X1 + K2 \times X2 + K3 \times X3 + K4.$$

In the equation described above, PD1 is a second fabric predicted feature value in the second fabric predicted feature value group, K1 is a first slope of the first straight line L1 divided by three, K2 is a second slope of the second straight line L2 divided by three, K3 is a third slope of the third straight line L3 divided by three, K4 is a summation of a constant term of the first straight line L1, a constant term of the second straight line L2 and a constant term of the third straight line L3, and X1, X2 and X3 are a main yarn percentage, a fabric weight and a drape coefficient of the second fabric, respectively.

In summary, by using the fabric feature predicting method 100, the third fabrics corresponding to the second fabric are selected from the known first fabrics, and the second fabric predicted feature value group of the second fabric is predicted according to the third fabrics. Compared to conventional approaches, the present disclosure can reduce time and cost for measuring the second fabric.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A fabric feature predicting method, comprising:
measuring first fabrics to generate first fabric actual feature value groups of the first fabrics;
storing the first fabric actual feature value groups and first fabric information groups of the first fabrics;
selecting third fabrics from the first fabrics according to a second fabric information group of a second fabric;
generating at least one equation according to third fabric actual feature value groups of the third fabrics and third fabric information groups of the third fabrics; and
generating a second fabric predicted feature value group of the second fabric according to the at least one equation and the second fabric information group,
wherein the first fabric actual feature value groups comprise the third fabric actual feature value groups, and the first fabric information groups comprise the third fabric information groups,
wherein:
each of the first fabric information groups comprises a main yarn percentage, a fabric weight and a drape coefficient of a corresponding one of the first fabrics, and
each of the third fabric information groups comprises a main yarn percentage, a fabric weight and a drape coefficient of a corresponding one of the third fabrics.

2. The fabric feature predicting method of claim 1, wherein
the second fabric information group comprises a main yarn percentage, a fabric weight and a drape coefficient of the second fabric.

3. The fabric feature predicting method of claim 1, wherein
each of the first fabric actual feature value groups comprises at least one of an actual meridional bending average stiffness, an actual zonal bending average stiffness, an actual meridional bending work, an actual zonal bending work, an actual thickness, an actual compression work, an actual compression recovery rate, an actual compression average stiffness, an actual recovery average stiffness, an actual thermal conductivity of compression, an actual thermal conductivity of recovery, an actual maximal heat flow, an actual meridional surface friction coefficient, an actual zonal surface friction coefficient, an actual meridional surface rough amplitude, an actual zonal surface rough amplitude, an actual meridional surface rough wavelength, an actual zonal surface rough wavelength of a corresponding one of the first fabrics, and
each of the third fabric actual feature value groups comprises at least one of an actual meridional bending average stiffness, an actual zonal bending average stiffness, an actual meridional bending work, an actual zonal bending work, an actual thickness, an actual compression work, an actual compression recovery rate, an actual compression average stiffness, an actual recovery average stiffness, an actual thermal conductivity of compression, an actual thermal conductivity of recovery, an actual maximal heat flow, an actual meridional surface friction coefficient, an actual zonal surface friction coefficient, an actual meridional surface rough amplitude, an actual zonal surface rough amplitude, an actual meridional surface rough wavelength, an actual zonal surface rough wavelength of a corresponding one of the third fabrics.

4. The fabric feature predicting method of claim 3, wherein the second fabric predicted feature value group comprises at least one of a predicted meridional bending average stiffness, a predicted zonal bending average stiffness, a predicted meridional bending work, a predicted zonal bending work, a predicted thickness, a predicted compression work, a predicted compression recovery rate, a predicted compression average stiffness, a predicted recovery average stiffness, a predicted thermal conductivity of compression, a predicted thermal conductivity of recovery, a predicted maximal heat flow, a predicted meridional surface friction coefficient, a predicted zonal surface friction coefficient, a predicted meridional surface rough amplitude, a predicted zonal surface rough amplitude, a predicted meridional surface rough wavelength, a predicted zonal surface rough wavelength of the second fabrics.

5. The fabric feature predicting method of claim 1, wherein selecting the third fabrics comprises:

comparing the second fabric information group and the first fabric information groups; and selecting, in the first fabrics, a part closest to the second fabric information group as the third fabrics.

6. The fabric feature predicting method of claim 5, wherein comparing the second fabric information group and the first fabric information groups comprises:

comparing a distance between the second fabric information group and one of the first fabric information groups in a vector space, wherein three axes of the vector space correspond to a main yarn percentage, a fabric weight and a drape coefficient, respectively.

7. The fabric feature predicting method of claim 1, wherein generating the at least one equation comprises:

generating N straight lines according to the third fabric information groups and the third fabric actual feature value groups; and generating one of the at least one equation according to N slopes of the N straight lines, wherein N is a positive integer.

8. The fabric feature predicting method of claim 7, wherein generating the N straight lines comprises:

generating a first straight line in the N straight lines according to main yarn percentages in the third fabric information groups;

generating a second straight line in the N straight lines according to fabric weights in the third fabric information groups; and generating a third straight line in the N straight lines according to drape coefficients in the third fabric information groups.

9. The fabric feature predicting method of claim 8, wherein the one of the at least one equation is:

$$PD1 = K1 \times X1 + K2 \times X2 + K3 \times X3 + K4,$$

wherein PD1 is a second fabric predicted feature value in the second fabric predicted feature value group, K1 is a first slope of the first straight line divided by three, K2 is a second slope of the second straight line divided by three, K3 is a third slope of the third straight line divided by three, K4 is a summation of a constant term of the first straight line, a constant term of the second straight line and a constant term of the third straight line, and X1, X2 and X3 are a main yarn percentage, a fabric weight and a drape coefficient of the second fabric, respectively.

\* \* \* \* \*